United States Patent [19]

Tipton, Jr.

[11] 4,015,135
[45] Mar. 29, 1977

[54] METHOD AND APPARATUS FOR PARTICULATE MONITORING

[75] Inventor: Douglas F. Tipton, Jr., Wilmington, Del.

[73] Assignee: E. I. DuPont de Nemours and Company, Wilmington, Del.

[22] Filed: Jan. 10, 1975

[21] Appl. No.: 539,982

[52] U.S. Cl. .............................. 250/574; 250/564; 356/102; 356/103
[51] Int. Cl.² ..................................... G01N 15/02
[58] Field of Search ........... 250/564, 574; 356/102, 356/103

[56] References Cited
UNITED STATES PATENTS

| | | | |
|---|---|---|---|
| 3,275,744 | 9/1966 | Dietrich | 356/102 X |
| 3,665,201 | 5/1972 | Shea et al. | 250/574 |
| 3,770,349 | 11/1973 | Legorreta-Sanchez | 356/102 X |
| 3,797,937 | 3/1974 | Shofner | 356/102 |
| 3,819,269 | 6/1974 | Duvall et al. | 356/103 X |

*Primary Examiner*—Eugene La Roche

[57] ABSTRACT

Method and apparatus for real time particulate monitoring in a fluid utilizing a laser directed at the suspended particle-containing fluid, two-dimensional multiple sensor radiation detector means receiving backscattered radiation from the particles generating electrical pulse signals representative of individual particle size and number, and means determining particle size distribution as a function of signal pulse height.

12 Claims, 10 Drawing Figures

U.S. Patent  Mar. 29, 1977  Sheet 1 of 8  4,015,135
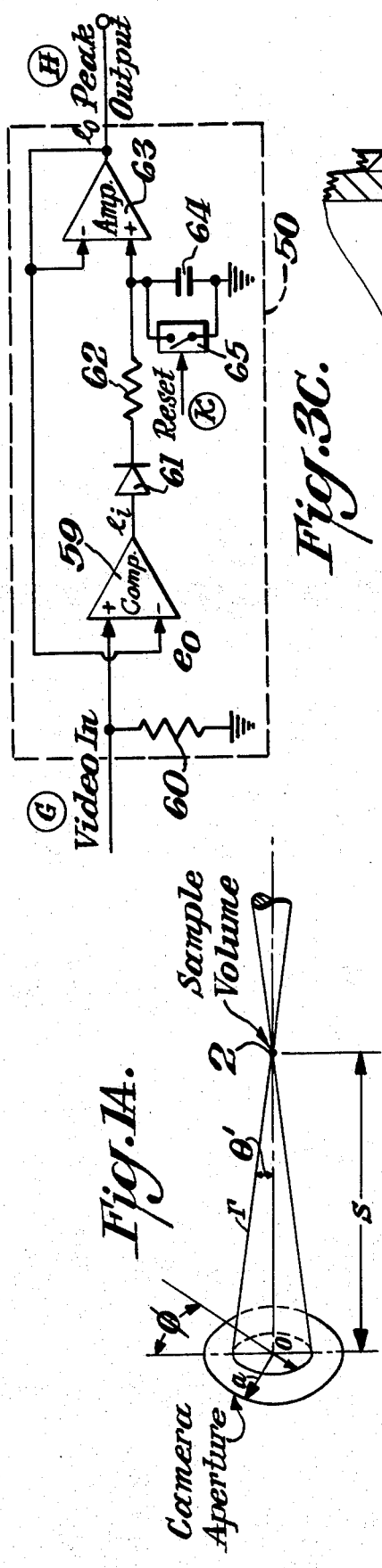
Fig.1A.
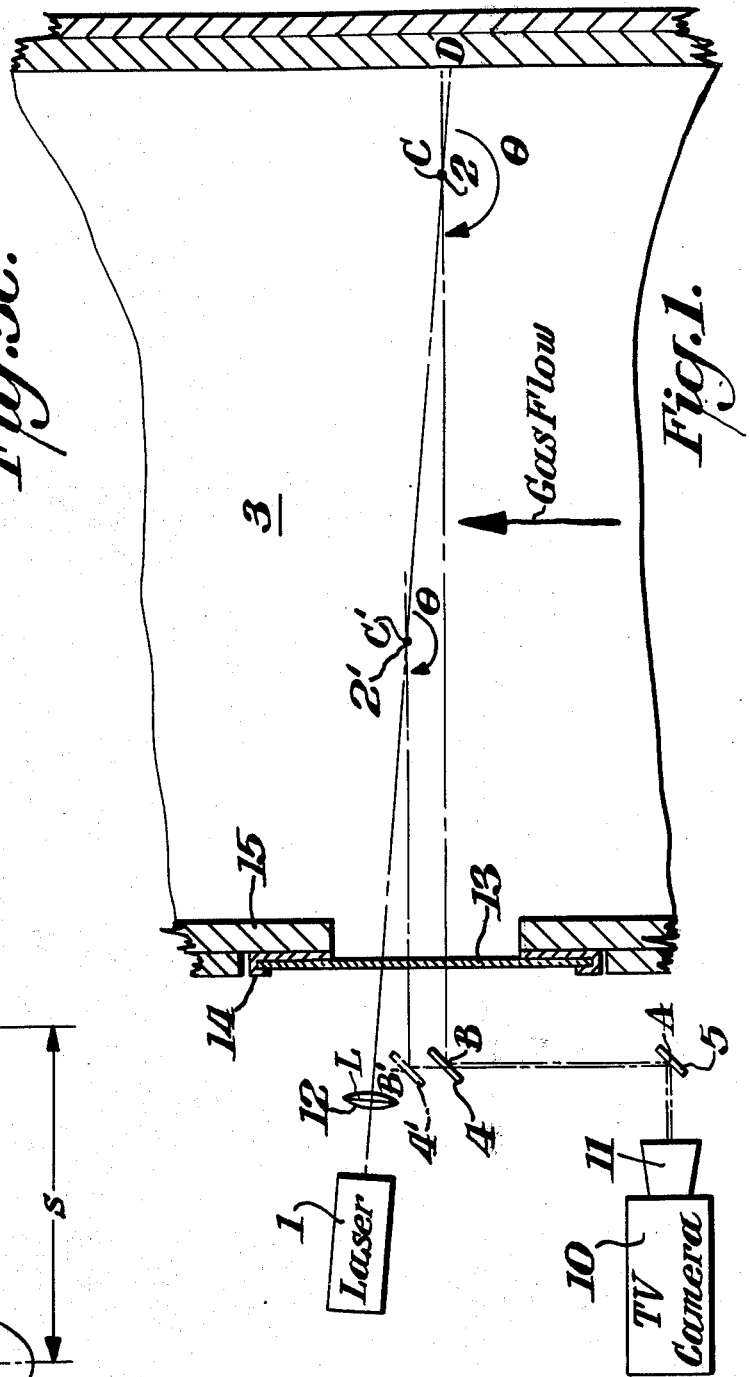
Fig.3C.
Fig.1.

Specific $\alpha$ Comparison Values
$\begin{cases} \alpha = 2.85 \text{ for a latex particle diam. } 0.481 \mu m \\ \alpha = 4.23 \text{ " " " " " } 0.714 \mu m \\ \alpha = 4.87 \text{ " " " " " } 0.822 \mu m \\ \alpha = 6.52 \text{ " " " " " } 1.1 \mu m \end{cases}$

METHOD AND APPARATUS FOR PARTICULATE MONITORING

BRIEF SUMMARY OF THE INVENTION

Generally, this invention relates to a method and apparatus for the classification according to particle size and number of fluid-suspended solid particles comprising illuminating a sample of the suspension having a predetermined known volume containing a particle population sufficiently small to permit substantially simultaneous back-scattered radiation measurement thereof for a given particle classification determination with a monochromatic light source, directing the essentially back-scattered radiation emanating from the sample to a two-dimensional multiple sensor radiation detector along a line substantially coincident with the optical axis of the detector, said detector transducing the back-scattered radiation from individual particles in the sample into electrical pulse signals, and determining particle size, number and distribution as a function of signal pulse height.

DRAWINGS

The following constitute part of this specification, in which:

FIG. 1 is a schematic representation of a preferred embodiment of the apparatus of this invention shown in operative relationship with respect to the cross section of a stack discharging combustion gases containing solid particles to be monitored, FIG. 1A is a diagram illustrative of the geometry of back-scattered radiation with respect to the camera aperture for the apparatus of FIG. 1, FIG. 2 is a block diagram of the apparatus of FIG. 1 showing the associated measuring circuitry, FIGS. 3A and 3A' together are a schematic diagram detailing the circuitry for one channel of the apparatus of FIGS. 1 and 2, FIG. 3B is a circuit diagram of an alternate design, employing peak detector and hold signal acquisition, which can be substituted for the circuit of FIGS. 3A and 3A', FIG. 3C is a circuit diagram of a preferred design of peak detector and hold circuit for the embodiment of FIG. 3B, FIG. 3D is a schematic representation of the waveforms in interrelated time relationship at various points in the circuit of FIGS. 3B and 3C, FIG. 4 is a typical log-log plot of Mie theoretical and experimental data for two solid particles-in-air systems wherein back-scattered radiation intensity is plotted as ordinate versus particle size parameter $\alpha$ as abscissa, with the Mie theoretical data shown in broken line representation, with the mean values depicted as a straight solid line and data points indicated, and FIG. 5 is a plot on the same axes as FIG. 4 for the experimental measurement of $TiO_2$ particles and latex spheres in water as the suspension medium.

BACKGROUND

Particulate-laden effluents, such as chimney stack gases and liquid waste streams, have caused concern for the public health and welfare, and regular reliable measurements of particle concentrations have become desirable and, in some cases, essential in order to meet permissible legislative standards. (The term "particle", as hereinafter used, is intended to comprehend both solids and liquid droplets suspended [including entrained ] in gas or liquid streams.)

However, apparatus is not now available which is capable of accurate, real time particulate measurements.

Thus, one Environmental Protection Agency-endorsed procedure specifies the use of a train type instrument which withdraws a sample of stack gas, after which the "catch" can be subjected to a particulate weight measurement and rough size determination therefrom. This takes approximately a day for the completion of a single instantaneous measurement and, also, the results are suspect, since simultaneous EPA train measurements have been found to vary by as much as a factor of four. Moreover, sample withdrawal is, in itself, a cause for measurement inaccuracy, since isokinetic (i.e., the same stack gas velocity) and isothermal (i.e., the same temperature) conditions are difficult to maintain.

Remote sensing techniques provide perhaps the only way to obtain a continuous valid record of particle size distribution statistics, in that this method does not require a sampling probe or the maintenance of isokinetic conditions during the sampling interval. However, known remote sensing apparatus based on optical phenomena (e.g., light transmission, scattering or absorption) are not easily transferred from one test location to another, nor are they easy to operate, nor do they operate reliably over an adequate range of particle sizes.

THE INVENTION

My invention utilizes the remote sensing of back-scattered radiation, which has the advantage that all of the monitoring equipment can be mounted compactly on a single side of the stack or effluent pipe in surveillance. This permits inspection of the effluent stream through only one viewing port per station, making it unnecessary to cut more than a single aperture in the waste stack or pipe.

Insofar as I am aware, the prior art does not teach effluent particle sizing using back-scattered radiation. The angular light scattering method, which is the closest approach to back-scattering utilized by the prior art, requires that several observations at various scattering angles be obtained in order to determine the relationship between scattering pattern maxima or minima and the particle size predicted by the Mie theory. It will be understood that this method is not easily automated and requires considerable data reduction to produce data of questionable validity.

The most serious deficiencies in previous remote sensing small particle sizing systems have included a failure to maintain a fixed sampling volume throughout an analysis period, and an inability to distinguish adequately the individual particles from conglomerates in large particulate concentrations, making correlations between theory and observation practically impossible.

The Mie back-scattering measurement apparatus of this invention utilizes a coherent monochromatic source, such as a pulsed xenon laser, to provide a collimated illuminating radiation beam. Back-scattered radiation is directed to a two-dimensional detector, broadly denoted in the claims as a multiple sensor radiation detector, which can, for example, be a TV camera so oriented and focused as to locate and view a well-defined volume size of analyte within the effluent stream. The laser pulse is synchronized with the TV camera vertical blanking signal, thereby obtaining frame-by-frame images of the particles within the sample volume. The camera scans these images on a line-by-line basis, thereby sensing the particle back-scattering intensities for subsequent measurement and sorting by a pulse height analyzer system and multi-channel readout.

The camera optical system is adjustable to provide the optimal image magnification necessary to (1) achieve spatial resolution between the scattering particles within the size range of interest, (2) establish the threshold of minimum camera sensitivity in order to prevent the back scatter within the range of interest from exceeding the dynamic range of the camera, and (3) limit the number of horizontal scan lines occupied by a single particle. In this manner, particulate concentrations up to almost complete opacity can be determined.

Since the camera field of view looks at more than one discrete angle of scattered radiation from the particles dispersed throughout the field of the frame "snapshot", an analysis "window" circuit is preferably provided to limit the line-by-line scan readout to the center of the field. In this way, the detected off-axis back scatter can be electronically masked to restrict particle size measurements to those appearing in the near vicinity of the precalibrated camera axis to permit more exact correlation of observed back scatter with particle size. FIG. 1a shows that, for a given sample-to-camera distance S, the camera aperture $a$ can be selected to limit the detected back scatter from the sample particles in sample volume 2 to a very small solid cone angle, typically 30' to one degree, for improved system sensitivity.

An additional feature of the apparatus is that, by knowing the pulse length of the laser beam and measuring the streak length produced by a particle on one camera frame, a rough measure of particle velocity can be obtained. This is useful information when deciding upon the location of the sample volume within the effluent stream for obtaining the most representative values of mass flow rates as a function of particle size. Preselection of the placement of the sample volume within the effluent is readily accomplished, without disturbing the angle between the camera and the laser beam axes, by means of an easily adjusted mirror system, all as hereinafter described.

The apparatus of this invention is versatile, compact, reliable and durable, and, in typical service where the particles are solids, is capable of small size particle monitoring in effluent streams having particle densities in the neighborhood of RINGELMANN 2 and below, wherein a reading of 2 signifies approximately 60% transmission (40% opacity), whereas a reading of 1 signifies approximately 80% transmission (20% opacity).

DETAILED DESCRIPTION

Figure 2:
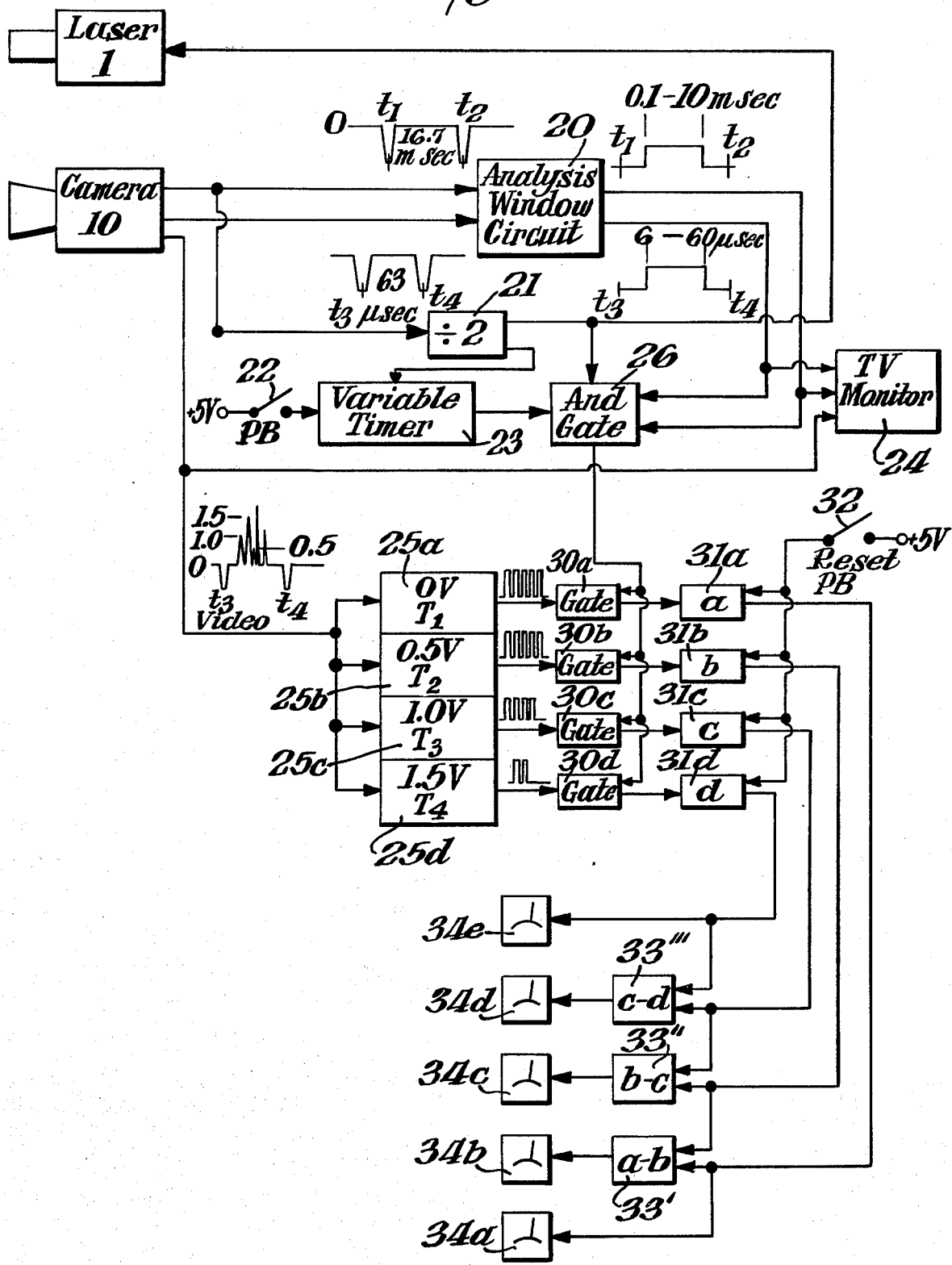

Referring to FIG. 1, there is shown in longitudinal section a typical smoke stack application of a particulate monitoring system wherein the laser radiation source 1 illuminates sample volume 2, which can be positioned optionally anywhere along the line segment LD within the vertically oriented stack 3 interior. Two such positions are denoted C and C', which correspond, respectively, to adjustable mirror 4 positions B and B'. From this it is seen that a translational adjustment of mirror 4 along the line ABB' preserves the scattering angle $\theta$.

Fixed plane mirror 5 directs the scattered radiation received from adjustable plane mirror 4 into a two-dimensional multiple sensor radiation detector, such as TV camera 10. Camera optics 11 consist of a combination of lens and aperture elements, not shown, required to focus on the sample volume, magnify the images to achieve spatial resolution of the scattering particles and adjust the received scattered intensity to an appropriate detector sensitivity level in order to maintain camera operation over a linear dynamic range of scattering intensities, typically over two orders of magnitude.

The camera optics can constitute, in series from mirror 5, a close-up lens, which can typically be any one of the following three: Canon Cu + 2 − 77, Tiffen + 1 − 77 or Tiffen + ½ − 77, all of which are 77 mm lenses of +2, +1 and +½ diopters, respectively. This is followed by a variable zoom lens, typically a Canon V 10 × 15, 150 mm focal length F 2.8 to 22, and then two range extenders, each of which can typically be a Canon EX − 2 × A 2 ×, which have a combined focal length equal to 600 mm.

Selection of a suitable close-up lens is dependent on the ojbect-camera distance. This is attached to the zoom lens, which is then rotated until the sample volume midpoint, as seen on the TV monitor 24 hereinafter described, comes into focus. If there is any blurring of the images due to saturation of the camera detector elements by intense back scattering, the zoom lens aperture is too large and a higher F stop should be substituted. In practice, the largest F stop practicable should be used, unless it is apparent that particles producing weak back-scatter signals are ineffective to cause the counters to step.

Focusing lens 12 concentrates the laser beam to an approximate one mm. diameter cross section at the sample volume point C (or C').

The viewing port assembly can comprise a 20.3 cm diameter heat resistant glass window 13 and a window mounting 14 secured to the duct wall 15 concentric with a 15.2 cm diameter port. Although these dimensions are not critical, the viewing port size must be sufficiently large to permit viewing sample volumes throughout the full cross section of stack 3.

The precise definition of the sample volume 2 about point C is a function of the depth of field, $\gamma_a$ based on the Rayleigh criterion, namely:

$$\delta_a = \left[ \frac{a^2 \lambda}{2(EFL)^2} \tan^2 \alpha_F \right] \cos \alpha_D \qquad (1)$$

where
  $\delta_a =$ is the depth of field,
  $a$ is the object distance from the camera,
  $\lambda$ is the illuminating wavelength,
  EFL is the effective focal length of the camera lens,
  $\alpha_F$ is the field of view,
and
  $\alpha_D$ is the angle subtended by the object distance off-axis as viewed at the camera lens.

Experiments have shown that typical depths of field range from 10-20 mm. (It will be hereinafter shown that the deleterious effect on depth of field of off-axis viewing is largely cured by the action of the camera analysis window control circuitry.) Sample volume size = $V_s$ = beam cross section $x$ depth of field $$V_s = \frac{\pi d^2}{4} \delta_u \qquad (2)$$

If the angular separation $\alpha_r$ necessary to resolve two adjacent particles in the field of view is based on the Rayleigh criterion:

$$\alpha_R = 1.22 \frac{\lambda}{W} \qquad (3)$$

where
 $\lambda$ is the illuminating wavelength, and
 W is the limiting aperture, then the closest theoretical resolvable distance between these particles is:

$$\text{resolvable distance} = EFL \times \alpha_r \qquad (4)$$

Typical experimentally obtained resolvable distances with the Xenon laser-TV system hereinafter described are on the order of 60 μm, using an EFL of 75 mm. and aperture W of 12.7 mm., whereas the Rayleigh criterion predicts about 4 μm. This difference is due to the fact that camera optics are not ideal.

Although the camera optical system is subject to a variety of influences tending to reduce the resolution and alter the intensity of the back-scattered radiation, most of these aberrations are dependent on the object distance off-axis and are cured by operation of the window control circuitry.

A variety of two-dimensional detectors, referred to generically herein as two-dimensional multiple sensor radiation detectors, can be used in this invention, including the TV camera tubes commercially available under the names "Plumbicon" and "Vidicon". The Plumbicon tube is preferred because of its enhanced sensitivity and lower lag time over a large range of irradiance values. However, the Plumbicon saturates at a somewhat lower face plate illumination level than the Vidicon.

Commercially available detectors include the RCA Vistacon 4591/G, the RCA Vidicon Model 8541 or Model 8507, and the Image Intensifier RCA Model 4804. Yet other sensors include the mosaics, such as Fairchild Camera & Instrument Co. Model CCD201, a 100 × 100 element area image sensor.

THEORY

Light scattering from small particles closely approximates the theoretical values obtained from Mie's solution of the boundary value problem posed by the scattering of an electromagnetic plane wave by an isolated homogeneous sphere [refer Light Scattering by Small Particles by Van deHulst (1957) Wiley, Principles of Optics by Born and Wolf (1970) Pergammon, and "The Scattering of Light and Other Electromagnetic Radiation" by M. Kerker (1969) Academic Press].

In effect, this formulation produces an exact scattering intensity, provided that values of the incident monochromatic radiation wavelength, intensity and polarization, scattering angle, the observer-particle distance, particle size, particle shape and refractive indices of both medium and particle are established. It is possible then to solve the reverse problem of determining particle size from the Mie formulation, provided that the incident and scattered intensities are known and the remaining parameters are either known or can be closely approximated.

As regards this invention, in order to preserve the simplicity of measurement and data reduction, the following parameters are listed as either known or assumed, with the bases for the assumptions hereinafter detailed:

| | | |
|---|---|---|
| $I_o$ = | intensity of incident radiation | - known |
| $I$ = | intensity of scattered radiation | - known |
| $\theta$ = | scattering angle typically 175° | - known |
| Polarization of the incident radiation | | - known |
| $\lambda$ = | wavelength in medium | - known |
| r = | observer - particle distance | - known |
| $m_1$ = | refractive index of medium | - assumed constant and known |
| $m_2$ = | refractive index of particle | - assumed constant and known |
| Particle shape | | - assumed spherical |
| Multiple scattering | | - assumed negligible |
| Effect of absorption of radiation by intervening particles along incident and scattering ray paths | | - assumed negligible |
| d = | particle diameter | - to be determined |
| Detector $\gamma$ (sensitivity) | | - assumed constant and known |

The normalized parallel and perpendicular intensity components of Mie scattered light are:

$$I\| = (\lambda/2\pi r)^2 i\| \cos^2\phi \qquad (5)$$

$$I\perp = (\lambda/2\pi R)^2 i\perp \sin^2\phi \text{ where} \qquad (6)$$

$\lambda$ is the wavelength of the radiation in the medium surrounding the scattering particle, r is the observer's distance from the scatterer, $i\perp$, $i\|$ are Mie intensity functions, perpendicular and parallel components, respectively, and $\phi$ is the angle of polarization of the incident plane wave E vestor with respect to the normal to the scattering plane, which contains the ray paths of the incident and scattered radiation. $I\|$, $I\perp$ are normalized intensity values with respect to $I_o$, emitted source radiation.

The involved mathematics utilized in the computation of Mie intensity functions is elaborated in Van de Hulst supra and is, accordingly, not further described here.

Applicant has made representative calculations for the Mie intensity function $i\perp$, particularly for values of refractive index $m = 1.50$, $\alpha = 1.0 - 10.0$ and $\theta = 180°$, 175° and 170°. Since the incident radiation is essentially perpendicularly polarized to the scattering plane for the applications of interest in this invention, only $i\perp$ values were computed and found to correspond closely to those tabulated in the literature (e.g., in Denman et al. "Angular Scattering Functions for Spheres", Wayne State University Press (1966) and McCormick et al. "Back Scatter Data", NASA TND-5110). Although there exist extensive tabulations of $i\perp$ and $i\|$ as functions of the parameters $$\alpha = ka = \frac{2\pi a}{\lambda},$$

$\beta$ = mka, and $\theta$, the precise behavior of these functions as a result of small changes in the independent parameters are better revealed by interactive computer graphing. (In the foregoing, $a$ = the particle radius (in meters), $k$ is the incident radiation propagation constant in radians/meter and $m$ is the relative refractive index between the scattering particle and the medium).

Study of the plots of these functions has shown that, for small changes in refractive index or angle of observation, $\alpha$ remaining constant, quite large variations in the Mie intensity functions can occur over some ranges. Consequently, it is essential that a source wavelength be selected which is adapted to produce $\alpha$ values which minimize such variations while still remaining within the sensitivity dynamic range of the camera 10.

Figure 4:
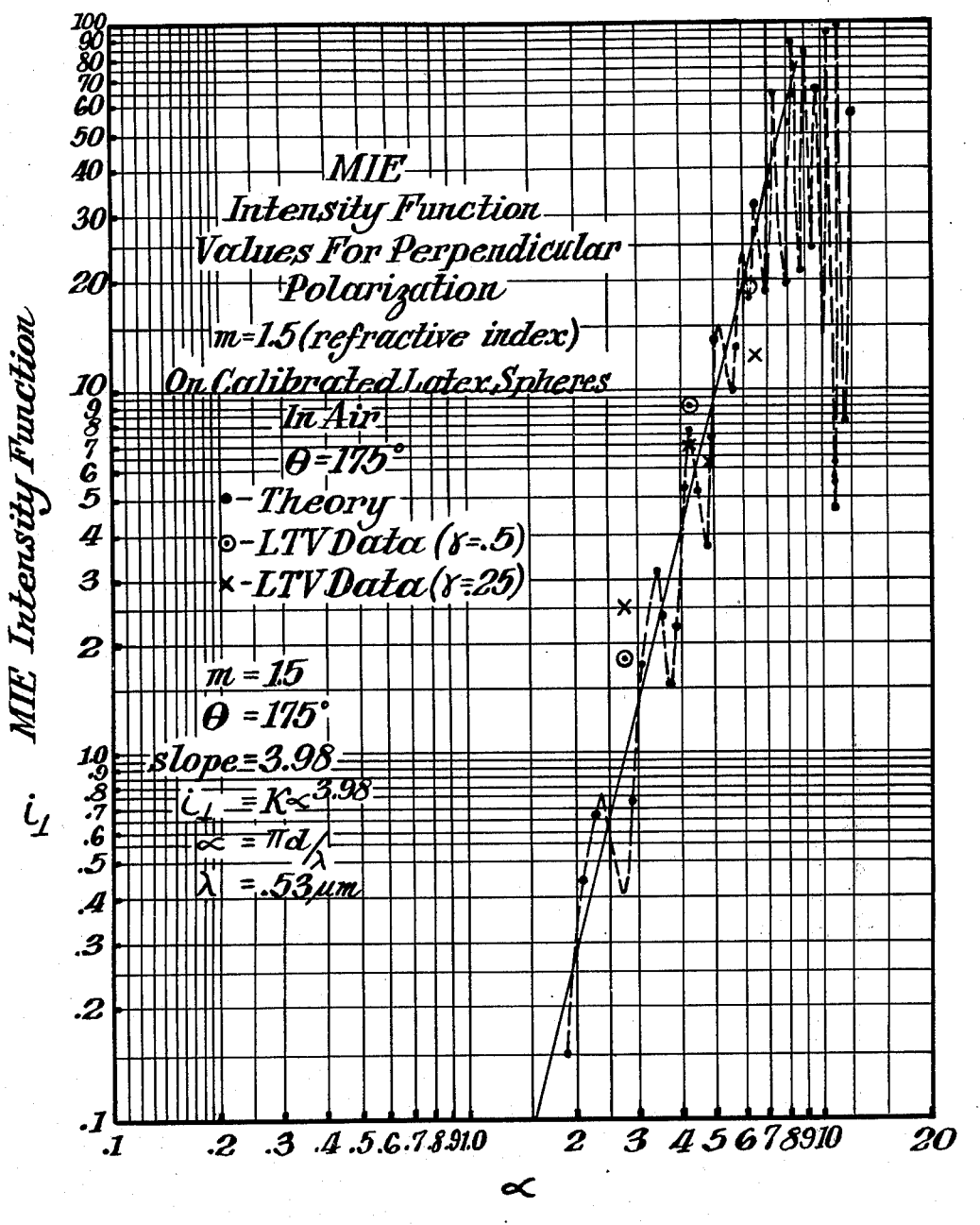

Using this approach, FIG. 4, for example, shows that the intensity function can be made directly proportional to $\alpha^n$, where $n$ equals 3.98 in this case. Theory shows that the exponent $n$ will vary between about 2.5 and 4.0 for particle sizes in the range of $\alpha = 0.5$ to 20, having relative refractive indices $m = 1.33$ and 1.5 and scattering angles of $\theta = 170°$–$180°$. The proportionality constant remains remarkably fixed at $K = 0.01$ over the stated ranges. As a general rule, it might be stated that particles with $\alpha >> 1$ give a light scatter proportional to $\alpha^2$, whereas, for $\alpha << 1$, the amount of light scattered is proportional to values ranging from $\alpha^4$ to $\alpha^6$.

In addition, I have observed that the scattering intensity increases smoothly with increasing $\alpha$ up to a maximum intensity at $\alpha = 1$. For larger $\alpha$, the intensity function exhibits a long series of irregular maxima and minima, typically oscillating about a value approximately one half that of the individual local peak intensities. At back scatter angles, these local maxima and minima values are each spaced apart about 1.0 $\alpha$ unit. Incidentally, light absorbing particles damp these oscillations and, in practical cases, the fluctuations are further smoothed by polydisperse distributions of $\alpha$.

Knowledge of the behavior of these curves attributable to changes in the parameters of interest are important not only to achieve an understanding of the scattering process but also to provide information necessary to establish a camera $\gamma$ value needed to convert the detected scattering intensity information directly into particle size video voltage values (V).

The functional equation used to obtain particle size from scattered intensity is $$V = W^\gamma = (Kd^n)^\gamma \tag{7}$$

where illuminance $W = f(d, \theta, \lambda, m, I_o, \text{ and } r)$.

Since $\theta, \lambda, m, I_o$ and $r$ are constant during a particular analysis, the latter relation becomes:

$$W = Kf(d) \tag{7a}$$

where overall constant K lumps all the constant parameters together. Furthermore $f(d)$ approximates $d^n$ in the range of interest, where n is the slope of the straight line shown in FIG. 4. If $\gamma$ is set equal to the reciprocal of the slope, $1/n$, then the particle diameter is directly related to video voltage, V, and:

$$d = K^{-1/n} V = K'V \tag{8}$$

DESCRIPTION OF CIRCUITRY

Referring to FIG. 2, there is shown a block diagram of an apparatus according to this invention utilizing a laser-TV camera timing and control system, characteristic waveforms being drawn in at appropriate points.

The vertical and horizontal blanking signals produced by TV camera 10 are inputs to the analysis "window" circuit 20. This circuit operates to produce an adjustable window frame within the bounds established by typical 16.7 m sec. vertical and 63 $\mu$ sec. horizontal scan signal inputs in order that only a selected portion of the video frame will be subject to analysis. As shown in the FIGURE, the waveforms at the analysis window circuit 20 output correspond to an analysis rectangle which is 0.86 screen widths long and 0.59 screen widths high. With the image of sample volume 2 centered on the face of TV camera 10, the analysis window circuit 20 operates effectively to limit the aberrations and changes in depth of field hereinbefore mentioned in order that the measurement of back-scattered intensity accurately reflect particle size.

In addition to activating the analysis window circuit 20, the vertical blanking signal causes the divide-by-two R/S (i.e., set-reset) flipflop 21 to produce a high logic output which is used to trigger laser 1 in synchronism with alternate scans of the scanning beam of camera 10. This permits the image appearing on the face of camera 10 to dissipate before the occurrence of the next laser 1 pulse, thereby eliminating the possibility of counting the same particle image twice. The logic low output from R/S flipflop 21 is connected to variable timer 23 which is activated by push button switch 22. The variable timing interval is selectable by the operator to permit counting over a wide range of particulate densities.

The video output signal from camera 10 and the horizontal and vertical window signals from analysis window circuit 20 are used to produce a visual display of the window region on TV monitor 24 once every 1/60th of a second.

As hereinbefore described, the camera 10 video signal is directly related to the $\gamma$ power of the camera 10 face plate illumination, under which circumstances, if $\gamma$ is preselected to have a value of $1/n$, where $n$ is the exponent of particle diameter in the equation $I = kd^n$, $n$ being the same value as that in the expression ($I \perp = K\alpha^n$, then the video output signal will correspond directly to particle size. Typical values of video output signal, which remain within the linear response range of camera tube 10, lie within 0 to 2.2 volts.

Comparators 25a – 25d operate in parallel to compare the video output signal levels with preset threshold levels denoted in the FIGURE. Only four comparator stages are shown; however, it will be understood that any convenient number can be provided to separate preselected signal levels into a corresponding number of individual channels. As represented in the FIGURE, the digital signal outputs from comparators 25a – 25d correspond to video signal amplitudes which exceed the preselected minimal voltage level just above 0 v. for the first threshold. This, together with the succeeding 0.5 v., 1.0 v. and 1.5 v. thresholds shown schematically, separate the several signals according to differences in amplitude values.

AND gate 26 operates to produce a logic high level control pulse, allowing the discriminated particle-related signals to pass from comparators 25a – 25d to the counting section through the corresponding parallel operating AND gates 30a – 30d upon the simultaneous occurrence of the following events: (1) a counting signal from timer 23, (2) a logic high signal from R/S flipflop 21 and (3) the presence of horizontal and vertical window signals from analysis window circuit 20. Thus, AND gate 26 ensures that a particle count will take place only when the video output signal relates to camera scans within the prescribed window frame, after the most recent laser 1 pulse.

Counter and D/A converter elements 31a – 31d, respectively, count the digital signals appearing at the output of AND gates 30a – 30d and convert these signals to analog voltages in order that the interchannel difference counts can be more easily obtained. Reset push button switch 32 is used to reset the counters at the end of the preselected timing interval established by variable timer 23.

Since the output values of elements 31a – 31d correspond to the respective counts of particles having signal amplitudes exceeding the threshold values set into comparators 25a – 25d, the particle count distribution within the channels defined by the threshold values of 25a – 25d is obtained through analog subtraction by operational amplifiers 33′, 33″ and 33‴ and displayed on the voltmeter indicators 34a - 34e, respectively.

Figure 3A:
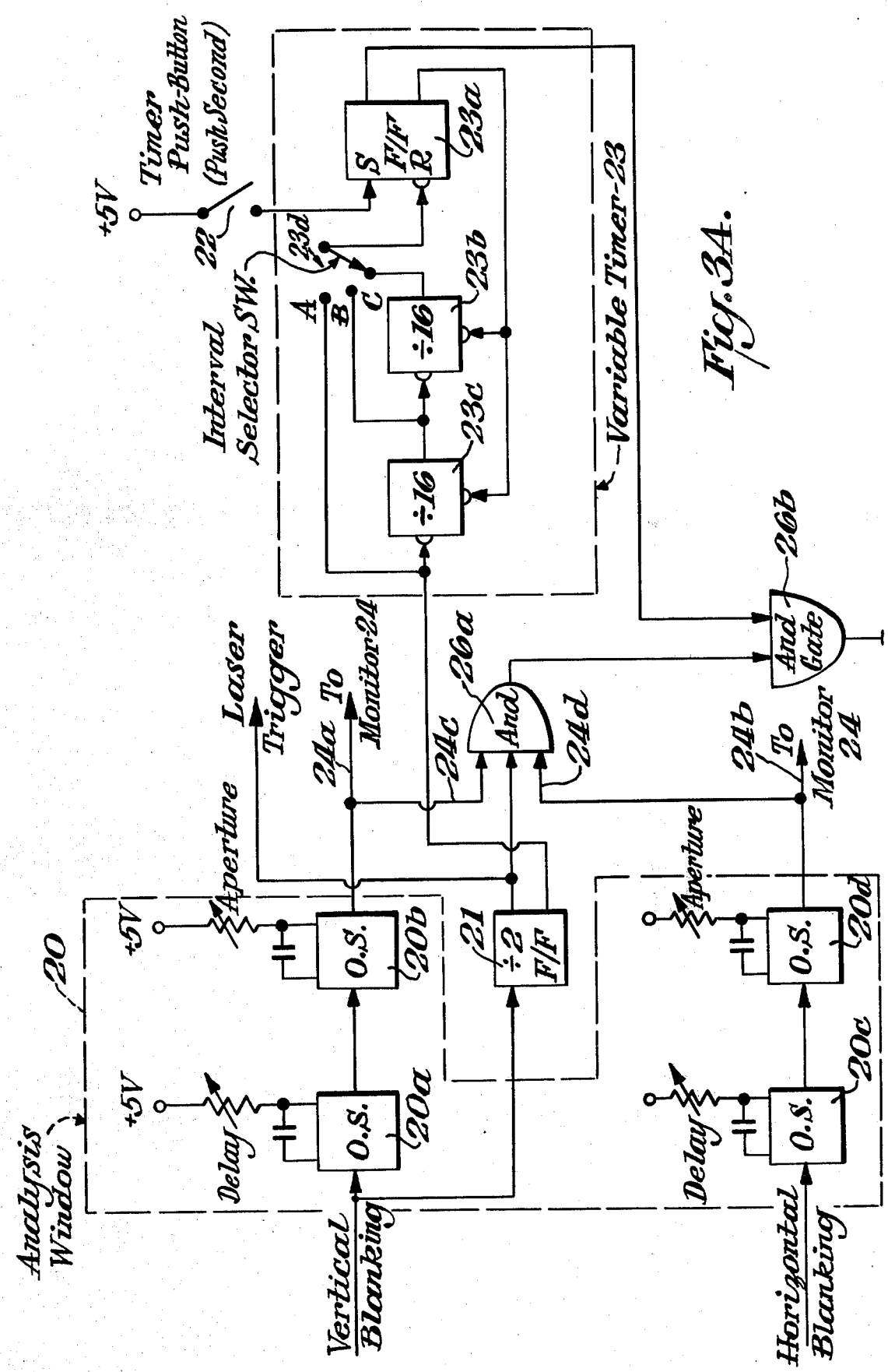
Figure 3A:
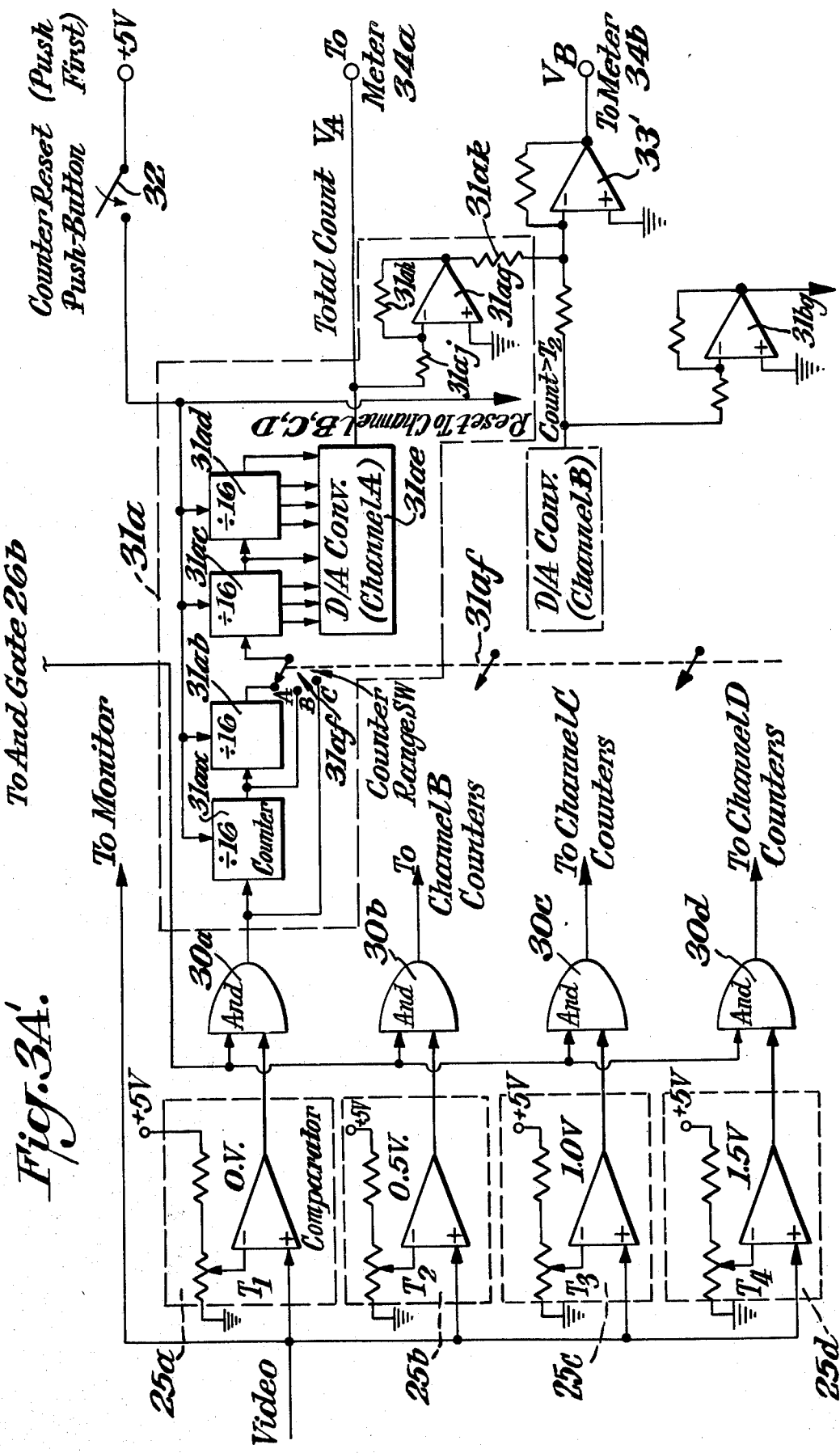

A preferred assemblage of equipment corresponding to the signal processing portion of the block diagram of FIG. 2 is detailed in FIGS. 3A, 3A′ and 3B, to which reference is now had.

Analysis window circuit 20, enclosed in the irregular block denoted in dashed representation, can embody two parallel-oriented pairs of one-shot multivibrators, constituting 20a, 20b and 20c, 20d, respectively, each of which is provided with a control subcircuit consisting of capacitors (e.g., 20a, 20b typically use 1.0 μ farad sizes, whereas 20 c, 20d utilize 0.005 μ farad sizes) on one side of each of which is provided a potentiometer (typically 50 Kohms) connected to a +5 v. source.

The 20a, 20b pair of one-shot multivibrators is reserved for the TV camera vertical blanking signal, whereas the 20c, 20d pair is reserved to the horizontal blanking signal, as indicated in FIG. 3A. Operation is as follows: the trailing edge of the vertical blanking pulse causes 20a to produce a rectangular pulse which has a duration set by the associated delay potentiometer. Similarly, 20c is activated by the trailing edge of the horizontal blanking signal and produces a corresponding rectangular pulse which has a duration predetermined by the setting of the delay potentiometer associated therewith. The leading edges of these two pulses activate one-shots 20b and 20d, respectively, which, in turn, produce the vertical and horizontal gating signals routed to the TV monitor 24 via lines 24a and 24b, respectively, and to AND gate 26a via lines 24c and 24d, respectively. The aperture potentiometers associated with one-shots 20b and 20 d define the dimensions of the analysis window, whereas both aperture and delay potentiometers are used to position the analysis window with respect to the camera axis. The TV monitor 24 (FIG. 2) permits the operator to position the window within the field of view and adjust its dimensions with respect to the sample volume.

Synchronization of the counting sequence with the laser trigger signal is effected by using the camera vertical blanking signal to toggle the divide-by-two flipflop 21. The logic high output signal at the upper output terminal of flipflop 21 triggers the laser 1 on alternate vertical blanking pulses and, together with the output signals of one-shots 20b and 20d jointly, control AND gate 26a. The output terminal of AND gate 26a connects with one of two input terminals of AND gate 26b.

The logic low signals produced at the lower output terminal of flipflop 21 step variable timer unit 23 on alternate frames and in synchronization with the laser trigger signal, as the lower output terminal of flipflop 21 is connected to the input terminal of counter 23c and contact A of interval selector switch 23d. The divide-by-sixteen counter 23c output terminal is connected to contact B of the interval selector switch 23d and the input terminal of counter 23b. The output terminal of counter 23b connects with contact C of selector switch 23d, whose arm is connected to the RESET terminal of flipflop 23a. The SET terminal of flipflop 23a is connected to a + 5 v. source through timer pushbutton 22. The timing interval is determined by the position of selector switch 23d, in that position A limits the count to a single frame interval, position B to an interval containing eight frames (0.25 sec.) and position C to an interval containing one hundred and twenty-eight frames (4.2 secs.). Depressing pushbutton 22 causes flipflop 23a to change state, whereby the logic low signal produced at the lower output terminal resets counters 23b and 23c, and the logic high signal at the upper output terminal passes to AND gate 26b. This signal remains at a high logic level until the end of the timing interval, at which time flipflop 23a is reset. In addition to constituting an input to TV monitor 24, the DC video output signal from camera 10 is simultaneously supplied to the inverting terminals of comparators 25a – 25d, which are separately biased using the individual series-connected 150 ohm resistors and 100 ohm potentiometers connected across the + 5 v. supply. This establishes threshold values $T_1 - T_4$, respectively, in order to amplitude-discriminate the particle-produced signals. The comparator outputs are connected to respective AND gates 30a – 30d which, in turn, control the stepping of respective counter elements 31aa – 31ad.

The output terminal of AND gate 26b is connected to the second input terminal of each of the AND gates 30a – 30d. It will be understood that count signals will pass through gates 30a – 30d only when all the signals at the input terminals of AND gates 26a and 26b have logic high values. Thus the pulses from comparators 25a – 25d will pass gates 30a – 30d only when the following conditions are satisfied: (a) a laser trigger signal has occured, (b) a window exists in the frame initiated simultaneously with the laser trigger signal and (c) the timer pushbutton 22 has been depressed.

A typical counter, 31a, constitutes four series-connected divide-by-sixteen individual counters 31aa, 31ab, 31ac and 31ad and ganged counter range selector switch 31af, such that the four bit output terminals of counters 31ac and 31ad connect to an eight bit D/A converter 31ae. Counter range switch 31af separates counters 31aa, 31ab from the remaining counters and provides selectable count scaling capability for the apparatus. Contact A is connected to the output terminal of counter 31ab, contact B is connected to the output terminal of counter 31aa, whereas contact C is connected directly to the output terminal of AND gate 30a. When the arm of switch 31af is set on contact C, the D/A converter 31ae can receive a maximum 256 count (i.e., 16 × 16), when set to contact B, a maximum 4096 count (i.e., 256 × 16), and when the arm is set to contact A, a maximum 65,536 count (i.e., 256 × 256) can be converted. Depressing pushbutton switch 32 resets all counters simultaneously in preparation for the next measurement interval.

The output terminal of D/A converter 31*ae* is connected to total count meter 34*a*. Since threshold $T_1$, for Channel A is typically set at a minimal level just above zero volts, meter 34*a* (FIG. 2) will display essentially all particle counts during the selected sampling interval as a function of the level of signal $V_A$. A unity gain inverting amplifier 31*ag*, provided with a 10 Kohm feedback resistor 31*ah*, is also connected to the D/A converter 31*ae* output terminal through a 10 Kohm load resistor 31*aj*. Amplifier 31*ag* inverts the Channel A signal for comparison, via load resistor 31*ak* (typically 10 Kohms), with the analog signal from Channel B, which can have an identical amplifier 31*bg*, and accessories. The Channel B signal has a smaller value, because threshold $T_2$ is typically set to 0.5 v.

The resulting voltage level is that existing at the inverting (−) terminal of unity gain amplifier 33*i*, which represents the inter-channel difference count (i.e., the number of particles having signal amplitudes less than $T_2$ but greater than $T_1$). The output terminal of amplifier 33' is connected to analog meter 34*b*, FIG. 2, furnishing a display of the number of counts of particles having a $T_2 - T_1$ size distribution within the sampling interval as a function of the level of signal $V_B$.

It will be understood that, while FIG. 3A' details only a single channel A, there actually are four individual circuits similar to that hereinbefore described, each of which serves the other channels, referred to herein as the B, C and D channels, via comparators 25*b* − 25*d*, their associated gates 30*b*, 30*c* and 30*d*, and counter and D/A converters 31*b* − 31*d*, respectively.

ALTERNATE FIG. 3A' CIRCUIT

Figure 3B:
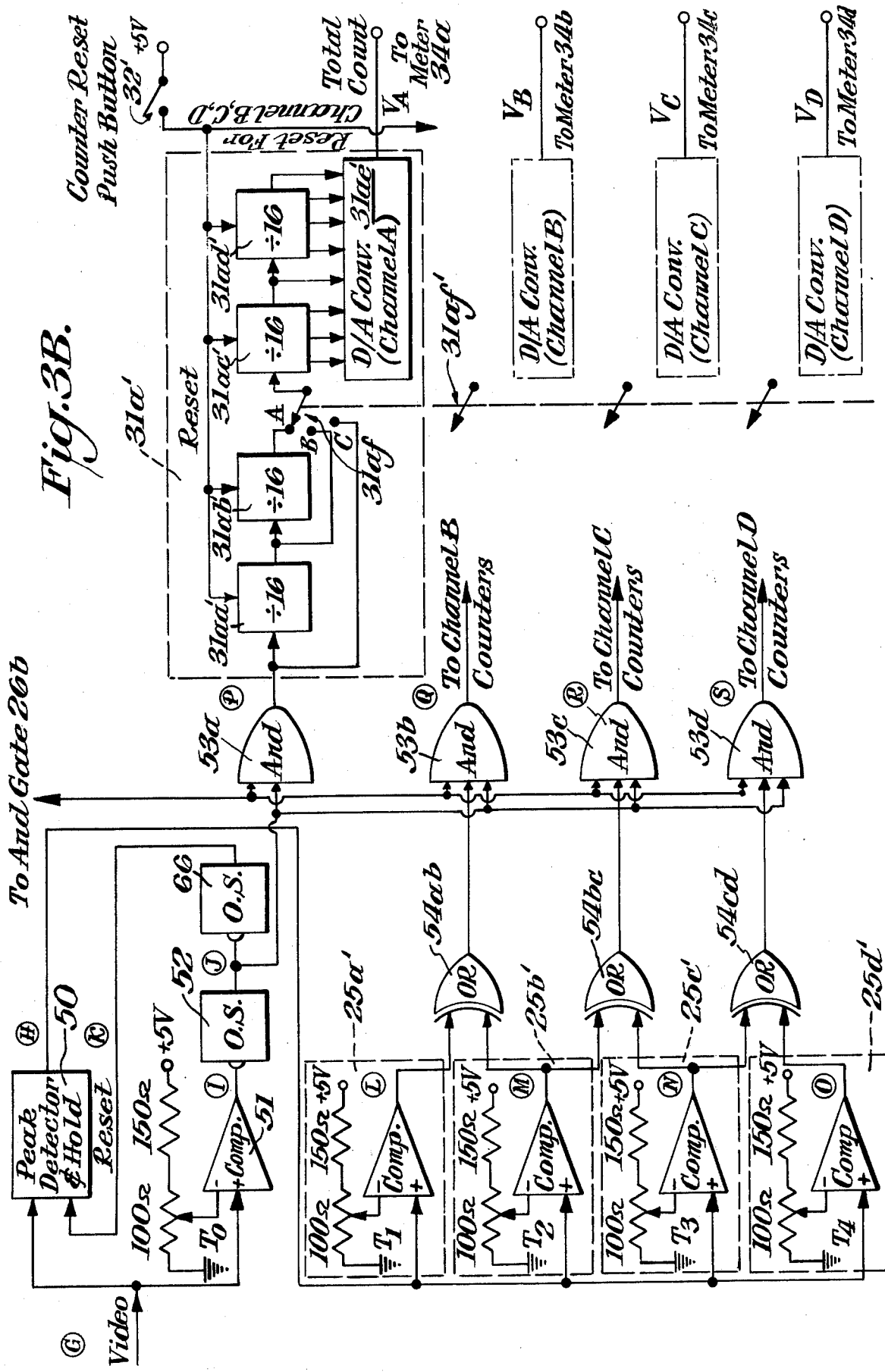

An alternate circuit which can sometimes be advantageously substituted for that of FIG. 3A' is shown in FIG. 3B. This utilizes a conventional peak detector and hold circuit 50, which permits elimination of analog signal subtraction employing the circuit elements 33', 33" and 33''', inclusive, and also simplifies the circuit following D/A converters 31*ae* − 31*be* of FIG. 3A'.

Again there is employed the same set of four comparators 25*a'* − 25*d'*, each with its own bias-setting potentiometer, identical with those shown in FIG. 3A'. However, now the video signal is provided via peak detector-hold circuit 50, which is reset as hereinafter described by a comparator 51 and one-shot multivibrators 52 and 66 after the occurrence of each signal peak. The output of comparator 51 is routed via one-shot element 52 to AND gates 53*a* − 53*d*, corresponding to AND gates 30*a* − 30*d* of FIG. 3A', and OR gates 54*ab*, 54*bc* and 54*cd* are interposed in series circuit between the paralleled outputs of the several comparator pairs 25*a'*− 25*d'* and AND gates 53*b* − 53*d*.

The individual outputs of AND gates 53*a* − 53*d* are routed to individual counter and D/A converter elements 31*a'*− 31*d'*, respectively, which can be identical with those of FIG. 3A', except that unity gain inverting amplifiers, such as 31*ag* and their accessories, are no longer utilized and thus can be dispensed with.

With the apparatus of FIG. 3B, the four distinctive counts are the outputs of the respective counter and D/A converter apparatuses which pass, as total count, to meter 34*a*, channel B count to meter 34*b*, channel C count to meter 34*c* and channel D count to meter 34*d*.

Referring to FIG. 3C, the peak detector and hold circuit 50 is detailed in full and comprises a comparator configured amplifier 59 (typically a PHILBRICK 1430), the input of which is dropped to ground through resistor 60 (typically, 100 ohms). The binary signal voltage $e_i$ passes thence through diode 61 (typically a IN916) and resistor 62 (typically 50 ohms) to the positive input of a buffering operational amplifier 63 (typically a PHILBRICK 1430). Amplifier 63 is connected in unity gain mode by feedback of its output voltage $e_o$ to its negative input terminal. In addition, $e_o$ is applied as a reference level at the negative input terminal of comparator 59. Signal holding is effected by capacitor 64 (typically 0.001 $\mu$f) connected between the positive input terminal of amplifier 63 and ground. Capacitor 64 is shunted by reset switch 65 (i.e., a FET, e.g., a Crystallonics CAG 10) which is automatically actuated as hereinafter described.

Figure 3D:
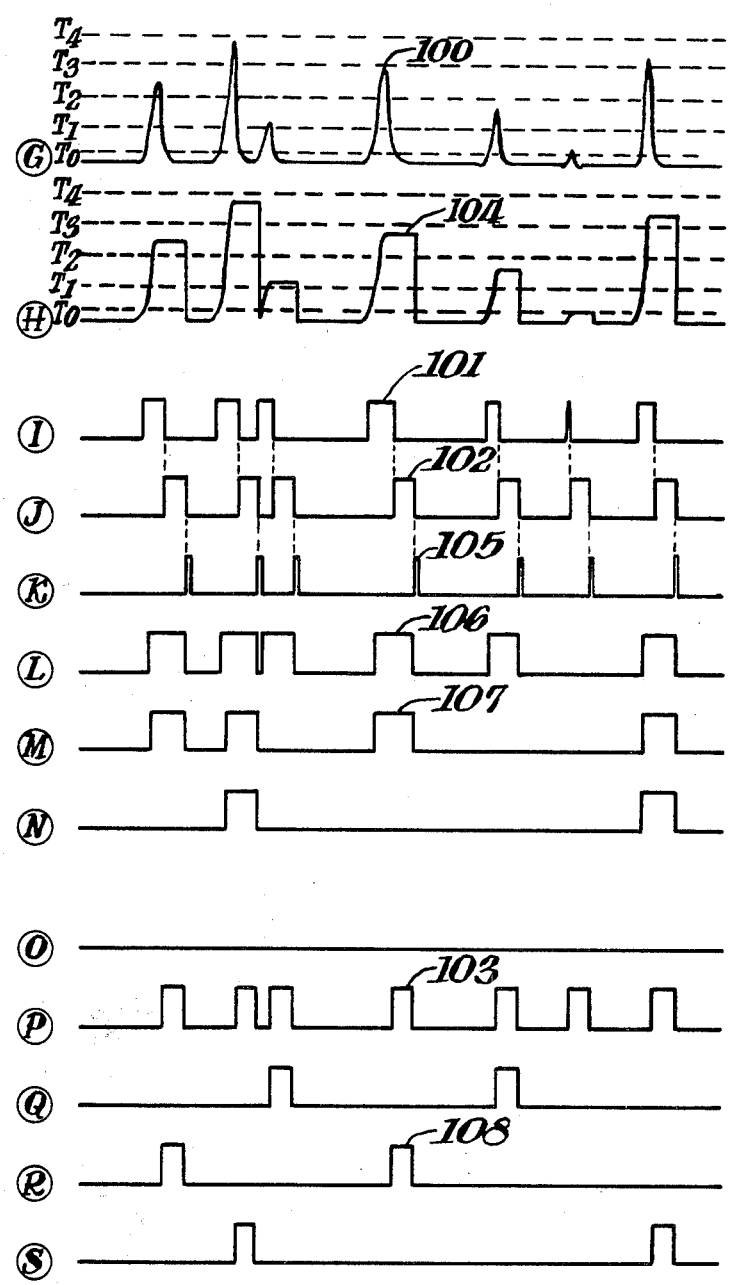

FIG. 3D is a schematic representation of the voltage waveforms at points indicated by encircled letters at different points in the circuits of FIGS. 3B and 3C.

In operation, the alternate circuit functions as follows:

A measurable pulse from the video output is detected by comparator 51 whose output remains high during the time the pulse amplitude exceeds a near zero minimal voltage reference level. During this time, peak detector capacitor 64 charges up to the peak value of the pulse and holds that value, since the combined action of buffer amplifier 63 and diode 61 blocks the flow of charge out of this capacitor on the signal downswing. Comparators 25*a'* − 25*d'* in circuit with the output of peak detector 50 fire as their respective reference levels are exceeded, and remain fired for as long as the peak detector 50 output is held. When the pulse amplitude falls below the near zero minimal reference level, comparator 51 output goes to a logic low level and causes one-shot 52 to trigger a short gate pulse J signaling that the comparator outputs are ready for interrogation.

The outputs of adjacent comparators 25*a'* − 25*d'* are connected to the inputs of logical "exclusive OR" gates 54*ab*, 54*bc* and 54*cd* whose outputs will be logical one (high) if one or the other (but not both) inputs are one (high). The OR gate outputs are transmitted to their respective counters 31*b'* − 31*d'* via gates 53*b* − 53*d* during the J pulse. If the OR output is one (high) during the gate pulse, the associated counter 31*b'* − 31*d'* will increment one count. Following the gate pulse, a second one-shot multivibrator 66 is triggered, which produces a control pulse K discharging capacitor 64 by momentary closure of reset switch 65.

To summarize, pulse 100 of waveform G, FIG. 3D, for example, has a peak which falls between thresholds $T_2$ (typically, 1.0 v.) and $T_3$ (1.5 v.). Comparator 51 with a minimal near-zero voltage threshold setting, outputs a pulse 101, waveform I, and triggers a one-shot 52 pulse 102 waveform J to output a count pulse 103 waveform P in total count counter 31*a'*. In the meantime, peak-detect and hold circuit 50 generates the hold-peak signal pulse 104, waveform H (as reset by pulse 105 waveform K) and becomes an input signal simultaneously to comparators 25*a'* − 25*d'*. Since pulse 104 has exceeded both thresholds $T_1$ (0.5 v.) and $T_2$ (1.0 v.) set into comparators 25*a'* and 25*b'*, respectively (pulses 106 and 107 waveforms L and M), exclusive OR gate 54ab prevents the receipt of a count by 0.5 v. counter 31b' (waveform Q). However, since comparator 25c' does not fire (waveform N) exclusive OR gate 54bc permits pulse 108, waveform R (originated as pulse 107 waveform M from 25b') to increment the 1.0 v. counter 31c'. Neither comparator 25c' nor succeeding comparator 25d' fire, so 1.5 v. counter 31d' will not be incremented. Since the counters can increment simultaneously, a real time tally of particle size distribution is achieved.

CALIBRATION

Due to the complexity of the scattering process and the sensitivity of the optical and electronic components required, it is preferred to calibrate the monitoring system of this invention against particles having known size and optical properties which most nearly represent the particulate characteristics encountered in the proposed utilization. One commonly available calibrating aerosol which is useful for fly-ash monitoring contains monodispersed (i.e., identical particle size) polystyrene latex (PSL) spheres. These have a refractive index $m = 1.6$, are obtainable in a range of sizes from 0.088 to 1.305 $\mu$m and exhibit small variance about the mean particle size, usually less than 5%. A commercially available aerosol generator, such as ROYCO MODEL L256, marketed by Royco Instruments, Inc., Menlo Park, California, is capable of producing calibrating aerosols for threshold adjustment to particular in situ applications.

Log-Log plots, such as that of FIG. 4, show that the scattering intensity from a single particle is a multiple-valued function of the size parameter $\alpha$, and, because of this, in most regions of the scattering curve, values of scattering intensity do not relate to unique values of particle size. However, research reveals that minimum changes in scattering intensity with observation angle $\theta$ occur in the forward and back scatter directions regardless of changes in refractive index and particle size. Thus, FIG. 4 shows that a characteristic straight line can be drawn through the mean of the points with a slope between about 2.5 and 4.0, dependent on the angle of observation $\theta$, the range of $\alpha$ values and the relative index of refraction, $m$.

With the straight line established, the two-dimensional detector $\gamma$ can be set to the reciprocal value of the slope of the characteristic straight line for $\theta = 175°$, typically and $m = 1.6$ for PSL spheres, whereupon the observed normal distribution of particle sizes about the mean value of the calibrating aerosol lies close to this line. This makes it possible to set channel threshold values which remain essentially valid over the linear range of detector sensitivity ($\gamma$), provided that the laser-TV system is operated over a range of particle sizes which remain outside regions of excessive multivaluedness. If necessary, the wavelength of the radiating source can be changed in order to ensure that the apparatus operates in the most predictable region of the scattering curve.

The literature (e.g., A. C. Holland and J. S. Draper, "Analytical and Experimental Investigation of Light Scattering from Polydispersions of Mie Particles", Applied Optics, Vol. 6, No. 3, March 1967, pp. 511–518) provides support for the fact that the volume (or mass) scattering coefficient for a polydisperse (i.e., particles of different sizes) system of irregular but randomly oriented particles shows a remarkable similarity to the corresponding scattering coefficient for spheroidal particles. Consequently, irregularities in particle shape do not seriously affect measurements of particle size with the apparatus of this invention if an aerosol containing spherically shaped particles has been employed to obtain calibrated threshold levels. In fact, experimentation shows that a heterogeneous matrix of particles of the same relative refractive index m tends to reduce the fluctuations appearing in the theoretical curves of single spherical particle scattering.

The opacity of the effluent stream affects the determination of particle size, since multiple scattering and intervening particle absorption then become significant considerations for measurement accuracy. Intervening particle absorption occurs along the paths between the radiation source-sample volume-detector and causes the attenuation of scattering intensity by a constant factor over the entire range of particle sizes. In contrast, multiple scattering influences the back-scattered intensity in an unpredictable manner. This effect is observed in the vicinity of the sample volume as neighboring particles, which receive the incident radiation, reradiate this energy into the sample volume. The resulting scattered intensities fluctuate around their Mie values dependent on the phase and polarization of the interfering radiation. Limiting the size of the sample volume to a small sample space centered on the camera and laser optical axis reduces the influence of multiple scattering on measurements in an opaque effluent stream, whereas a simple correction scheme can be used to modify the discriminated values of scattering intensity as a function of particle size and concentration (opacity).

EXAMPLES

I. The objective here was to measure fly ash particulate distribution within a powerhouse smoke stack effluent, and to compare the results obtained with those of a conventional EPA train analyzer.

The apparatus utilized was constructed according to FIGS. 3A and 3A′, and embodied a xenon laser and a Plumbicon TV camera, the entire apparatus being installed on a platform to monitor effluent through a heat-resistant glass viewing port mounted in the wall of a transition duct disposed between an electrostatic solids precipitator (upstream) and the discharge stack (downstream). At this location, the stream velocity was about 10 meters/sec. and particulate concentrations ranged up to about 200 counts/mm.$^3$.

Prior to monitoring service, the apparatus was calibrated by conducting measurements on precalibrated PSL (polystyrene latex) spheres having a refractive index close to that of fly ash. The PSL spheres were entrained in an aerosol exhausted into the atomosphere from the outlet of a 6.35 mm. diameter tube attached to the output of a Royco generator. The velocity of the aerosol stream was about 1.52 meters/min., with particulate concentrations of about 15 counts/mm.$^3$. Sphere sizes measured included the following diameters, all in $\mu$m: 0.357, 0.481, 0.714, 0.822 and 1.1.

In monitoring the entrained fly ash, readings were taken at the following four points across the 7 ft. (213 cm.) diameter of the stack: 12 inch (30.5 cm.), 18 inch (45.7 cm.), 33 inch (83.9 cm.) and 62 inch (157 cm.) without difficulty. However, the specific test results hereinafter reported were those obtained at the 12 inch (30.5 cm.) position, in order to conform with the EPA apparatus installed position.

The laser peak power was varied from 300–400 and the camera tube aperture size adjusted wherever necessary to limit the scattering intensities to the linear portion of the TV camera dynamic characteristic. In addition, a 30 cycle/sec. laser pulse repetition rate was utilized to ensure that the laser illuminated each particle field viewed in sequence only once, under the existing effluent discharge velocity. A 0.5$\mu$ sec. pulse was found to be sufficiently small to permit rapid determination of particle size distribution.

The following tests required only 8 seconds' total time duration each, and all three readings of each were made simultaneously. The three tests were made under different boiler operating conditions, as follows: Test No. 1 was conducted during the time that the electrostatic precipitator for fine particles (i.e., <4.0$\mu$m) was disabled; Test No. 2 was conducted after the precipitator had been restored to normal operation and stability had been achieved, and Test No. 3 was conducted with a normally operating precipitator, but when a richer fuel-air mixture was combusted than during Test No. 2.

The values denoted with a single asterisk (*) superscript are measured Total Loadings of Particulate Solids, whereas those denoted with a double asterisk (**) are EPA Train-Measured Total Loadings, all in grains/ft.$^3$.

| Instrument Reading | Channel Size Width ($\mu$m) | Median Particle Size ($\mu$m) | Count | Channel Wt (grain/ft$^3$) |
|---|---|---|---|---|
| TEST No. 1 | | | | |
| Channel A-Channel B | 2.15 | 1.6 | 655 | 0.0007 |
| Channel B-Channel C | 2.85 | 3.92 | 9,174 | 0.144 |
| Channel C-Channel D | 2.50 | 6.4 | 262 | 0.017 |
| | | | | 0.162* |
| | | | | 0.151** |
| TEST No. 2 | | | | |
| Channel A-Channel B | 1.25 | 0.935 | 0 | 0 |
| Channel B-Channel C | 1.69 | 2.28 | 17,693 | 0.048 |
| Channel C-Channel D | 1.45 | 3.74 | 524 | 0.006 |
| | | | | 0.054* |
| | | | | 0.054** |
| TEST No. 3 | | | | |
| Channel A-Channel B | 0.95 | 0.74 | 19,659 | 0.0018 |
| Channel B-Channel C | 1.31 | 2.0 | 32,765 | 0.0580 |
| Channel C-Channel D | 1.24 | 3.2 | 786 | 0.0056 |
| | | | | 0.065* |
| | | | | 0.076** |

Example I shows very good agreement between measurements obtained with this invention and those obtained with the EPA train. However, the EPA train measurements required a total of about 8 hours for analysis and interpretation, as compared with practically instantaneous read-out for this invention. Moreover, the EPA train is inconvenient to use, since one has to mount the sampling probe within the stack and, also, cannot change probe position easily in the event that testing at a different point, or several points in rapid sequence, is desired.

II. The objective here was to measure particulate solids suspended (or entrained) in a liquid carrier.

Several mixtures of TiO$_2$ particles of known size and latex (PSL) calibrating spheres were made up in H$_2$O and agitated by hand in circular movement to simulate fluid flow when viewed from the side.

The sample cell used to contain the sample solution consisted of an open parallelepiped having four 7.6.1cm × 2.54cm × .318cm optical quality quartz slabs glued around the periphery of a 2.54cm square base. After filling the cell with the sample solution, the laser beam was directed at a normal angle to one of the sample cell faces and focused at a point within the sample solution. In order to reduce the camera F/# and detect sufficient scattering intensity from the illuminated particles, the TV camera optics were placed within 2cm of the sample cell and oriented to observe the backscatter along a line at 165° angle from the incident beam. A 5× microscope eyepiece lens was used.

A secondary objective of this Example was to compare the measured results with those obtained from electron micrograph data.

As in the previous example, a xenon laser and a Plumbicon TV camera were installed on a platform to monitor the sample solution. In this example, a particle size distribution was obtained over ten channels as compared with the three channels of Example I.

Three sample solutions were prepared [one for the 0.415 $\mu$m TiO$_2$ particles, and two, respectively, for the 1.1 $\mu$m PSL and the 5.5 $\mu$m PSL particles, to make the TiO$_2$ concentration 600 particles/mm$^3$ (0.018 ppm Vol.) and the PSL sphere concentrations each 55 particles/mm$^3$ (3.4 ppm Vol. for 5.5 $\mu$m and 0.033 ppm Vol. for 1.1 $\mu$m)].

In order to obtain sufficient backscatter intensity from these particles at reasonably low laser input powers, and yet maintain a small sample volume size, a suitable measurement arrangement was obtained by (1) orienting the TV camera to view the backscatter along an angle of 165° from the incident beam and (2) using a 5× microscope eyepiece lens, positioning the TV camera optics approximately 2 cm from the nearest face of the sample cell. This arrangement was used for all of the following three tests.

The data obtained from Test No. 1 measurements on the agitated mono-disperse suspension of 1.1 $\mu$m size PSL calibrating spheres was used to calibrate the apparatus. Since the relative refractive index for the PSL spheres in water is $m = 1.1 - i0.05$, little scattering intensity was observed, even when using a laser peak power of 400 watts and a pulse width of 0.5 $\mu$ seconds. To measure the particulate size distibution, 252 "snapshots" were taken of the particle field and the resulting sub-totals of the channel difference counts were then averaged. The snapshots were taken with the laser firing at a rate of 30 times per second over a sampling interval of 8.4 seconds.

Using a sample volume size of 0.038 mm$^3$, a 2 particle count per sample volume could be expected.

Test No. 2 measurements were obtained on the polydisperse suspension of 3.9 to 7.0 $\mu$m (means diameter 5.5 $\mu$m) PSL calibrating spheres using the same set of test conditions as for Test No. 1.

Finally, for Test No. 3, measurements were obtained on the polydisperse suspension of 0.339 – 0.491 $\mu$m ( means diameter 0.415 $\mu$m) TiO$_2$ particles ($m = 2.0 - i0.05$) having sizes previously determined from electron-micrograph data. Since the scattering intensity from these latter particles was over two orders of magnitude greater than that from the PSL spheres (because of the higher refractive index of TiO$_2$), the laser input power was reduced to about 10 watts. Using a smaller sample volume size (0.0176 mm$^3$), but otherwise maintaining the sampling conditions used in the previous two tests, a 10.5 particle count per sample volume was anticipated.

| Instrument Reading | Channel Size ($\mu$m) | Test No. 1 1.1 $\mu$m PSL particle Count Per Sample Volume | Test No. 2 5.5 $\mu$m PSL particle Count Per Sample Volume |
|---|---|---|---|
| Channel A-Channel B | 0.5–1.0 | 40 | Overload |
| Channel B-Channel C | 1.0–1.5 | 2 | Overload |
| Channel C-Channel D | 1.5–2.0 | 0 | 90 |
| Channel D-Channel E | 2.0–2.5 | 0 | 6 |
| Channel E-Channel F | 2.5–3.0 | 0 | 2 |
| Channel F-Channel G | 3.0–3.5 | 0 | 1 |
| Channel G-Channel H | 3.5–4.0 | 0 | 0.5 |
| Channel H-Channel I | 4.0–4.5 | 0 | 0 |
| Channel I-Channel J | 4.5–5.0 | 0 | 0 |
| Channel J-Channel K | 5.0 and above | 0 | 2 |

| Test No. 3 Instrument Reading | Channel Size ($\mu$m) | TiO$_2$ Count Per Sample Volume |
|---|---|---|
| Channel A-Channel B | 0.04–.08 | Overload |
| Channel B-Channel C | 0.08–.12 | Overload |
| Channel C-Channel D | 0.12–.16 | Overload |
| Channel D-Channel E | 0.16–.20 | Overload |
| Channel E-Channel F | 0.20–.24 | 1 |
| Channel F-Channel G | 0.24–.28 | 3 |
| Channel G-Channel H | 0.28–.32 | 2 |
| Channel H-Channel I | 0.32–.36 | 1 |
| Channel I-Channel J | 0.36–.40 | 2 |
| Channel J-Channel K | 0.40 and above | 3 |

In interpretation of the test results tabulated it will be understood that the Test No. 1, Channel A – Channel B reading of 40 counts must be excluded, because it was due to extraneous radiation scattering. The Channel B – Channel C particle count of 2 is valid and conforms with the expected particle concentration based on the test solution as prepared.

Similarly, as to Test No. 2, the Channel C – Channel D count of 90 is to be excluded as due to extraneous source scattering, whereas the Channel D – Channel E count of 6 and the Channel E – Channel F count of 2 are both spurious, as due to signal-dependent noise, i.e., multiple counts. The remaining tabulated values must be added to give a total count of 3.5, the "0.5" being the result of averaging. Since the prepared solution was only approximate in particle content, this is considered acceptable conformity to the 2 particle content expected.

The total particle count of Test No. 3 is 12, which is certainly acceptable when compared with the 10 count predicted, especially since the sample was polydisperse and approximate in concentration to begin with.

Figure 5:
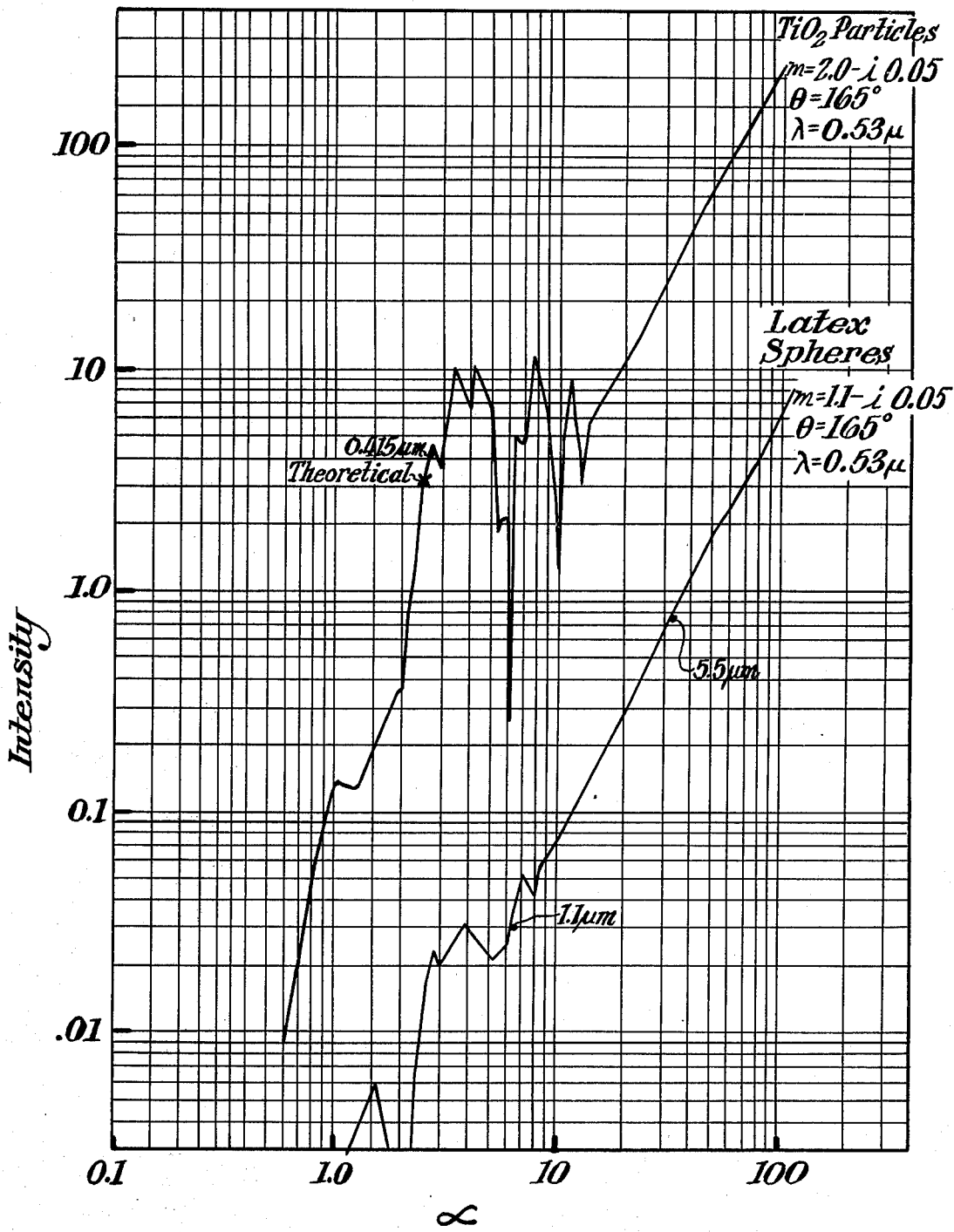

The results of Tests No. 1 – No. 3 are plotted in FIG. 5 against the computed Mie radiation scattering curves, and it is seen that all lie very near the curves, corroborating accuracy in the method of this invention.

What is claimed is:

1. Apparatus for the real time measurement of the size and number of fluid-suspended particles in general conformity with the Mie Theory comprising a pulsed monochromatic radiation source directing a collimated illuminating beam into the fluid suspension of said particles, means directing particle-scattered radiation to a two-dimensional multiple sensor radiation detector, and electronic means measuring in real time particle size and particle number responsive to said multiple sensor radiation detector, the pulse interval of said radiation source being preselected in time duration to afford complete examination of a given sample of said fluid suspension.

2. Apparatus according to claim 1 provided with optical focusing means interposed in the path of said particle-scattered radiation directed into said two-dimensional, multiple sensor radiation detector.

3. Apparatus according to claim 1 wherein said particle-scattered radiation is of the back-scattered type.

4. Apparatus according to claim 1 wherein said multiple sensor radiation detector is a television camera.

5. Apparatus according to claim 1 wherein said pulsed monochromatic radiation source is a pulsed laser.

6. Apparatus for the real time measurement of the size and number of fluid-entrained particles in a fluid stream according to claim 1 wherein said radiation source directing said collimated illuminating beam into said stream of said fluid-entrained particles is oriented generally transverse said stream.

7. Apparatus according to claim 6 disposed externally of said stream for the real time measurement of the size and number of fluid-entrained particles in transit through a fluid-confining conduit having at least one radiation-transmitting window in line with the radiation emission port of said radiation source and the path of said particle-scattered radiation in transit to said multiple sensor radiation detector.

8. Apparatus according to claim 1 wherein said electronic means measuring in real time said particle size and particle number is a pulse height analyzer provided with counting means for determining sub-totals of the number of said particles within preselected particle size ranges.

9. Apparatus according to claim 3 wherein the line of incident radiation is disposed from about 5° to about 15° to the line of back-scattered radiation from said fluid-entrained particles.

10. A method of measuring in real time the size and number of fluid-suspended particles in general conformity with the Mie Theory comprising directing a pulsed monochromatic beam of radiation into said suspension, collecting scattered radiation from said particles, transducing said scattered radiation into electrical pulses having characteristic heights and numbers which are real time functions of said particle size and said particle number, respectively, and obtaining a read-out of said particle size and number of said fluid-suspended particles.

11. A method of measuring in real time the size and number of fluid-suspended particles according to claim 10 wherein said readout is in terms of a preselected size classification.

12. In a method of measuring in real time the size and number of fluid-entrained particles according to claim 10, additionally measuring the approximate velocity of transit of said particles by pulsing said radiation source for a sufficient time duration to obtain displacement streaks associated with said particles and determining the time-rate of transit of said particles as a function of said pulsing time duration.

* * * * *

UNITED STATES PATENT OFFICE
CERTIFICATE OF CORRECTION

PATENT NO. : 4,015,135
DATED : MARCH 29, 1977
INVENTOR(S) : DOUGLAS F. TIPTON, JR.

It is certified that error appears in the above-identified patent and that said Letters Patent are hereby corrected as shown below:

Col. 3, line 65 - After "adjustable", insert --plane--
Col. 4, line 46 - "$\gamma$" should read --$\sigma$--
Col. 6, line 34 - "R" should read --r--
Col. 6, line 41 - "vestor" should read --vector--
Col. 7, line 67 - "K-1/n" should read --$K^{-1/n}$--
Col. 8, line 47 - Delete "("
Col. 11, line 22 - "33'i" should be --33'--
Col. 15, line 1 - After "400", insert --watts--
Col. 15, line 68 - "7.6.1" should read --7.61--
Col. 16, line 53 - "means" should read --mean--
Col. 16, line 58 - "means" should read --mean--

Signed and Sealed this nineteenth Day of July 1977

[SEAL]

Attest:

RUTH C. MASON
Attesting Officer

C. MARSHALL DANN
Commissioner of Patents and Trademarks